(12) United States Patent
Yazawa et al.

(10) Patent No.: US 7,888,708 B2
(45) Date of Patent: Feb. 15, 2011

(54) EXAMINATION APPARATUS FOR BIOLOGICAL SAMPLE AND CHEMICAL SAMPLE

(75) Inventors: Yoshiaki Yazawa, Nishi-Tokyo (JP); Kazuki Watanabe, Kokubunji (JP); Masao Kamahori, Kokubunji (JP); Yukinori Kunimoto, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 47 days.

(21) Appl. No.: 11/976,831

(22) Filed: Oct. 29, 2007

(65) Prior Publication Data

US 2008/0061323 A1    Mar. 13, 2008

Related U.S. Application Data

(62) Division of application No. 10/933,339, filed on Sep. 3, 2004, now abandoned.

(30) Foreign Application Priority Data

Jan. 21, 2004    (JP) .............................. 2004-012596

(51) Int. Cl.
*H01L 29/66* (2006.01)
(52) U.S. Cl. ................. 257/253; 257/409; 257/E29.013
(58) Field of Classification Search ......... 257/252–253, 257/409, 414, 452, 484, 490, 494–495, E29.012, 257/E29.013; 438/1, 48–49
See application file for complete search history.

(56) References Cited

U.S. PATENT DOCUMENTS 4,180,771 A    12/1979    Guckel 4,903,099 A    2/1990    Sekiguchi et al.

(Continued)

FOREIGN PATENT DOCUMENTS

DE    43 08 081 A1    3/1993

(Continued)

OTHER PUBLICATIONS

Tsukada K. et al., "A Multiple-ISFET Integrated with CMOS Interface Circuits", Electronic and Communications in Japan, Part 2, vol. 71, No. 12, 1988, XP 000036561, pp. 93-98.

(Continued)

*Primary Examiner*—Matthew W Such
(74) *Attorney, Agent, or Firm*—Stites & Harbison, PLLC; Juan Carlos A. Marquez, Esq.

(57) ABSTRACT

A wireless sensor chip suitable for the compact, high-sensitive, and low-cost examination apparatus for easily examining a biological material such as gene at low cost is provided. A sensor chip is formed on an SOI substrate, and an n type semiconductor layer on which a pMOS transistor is formed and a p type semiconductor layer on which an nMOS transistor is formed are isolated by a pn junction. Therefore, the p type semiconductor layer at the outermost portion (chip edge portion to be in contact with solution) is set to floating, and the maximum potential and the minimum potential of the chip are supplied to an n type semiconductor layer and a p type semiconductor layer inside the outermost portion, respectively. Also, the chip is covered with an ion impermeable insulating film for reducing the penetration of positive ions through the oxide layer.

8 Claims, 19 Drawing Sheets

U.S. PATENT DOCUMENTS

| | | | |
|---|---|---|---|
| 4,961,833 A * | 10/1990 | Sakai et al. | 257/253 |
| 5,138,251 A | 8/1992 | Koshiishi et al. | |
| RE34,893 E * | 4/1995 | Fujii et al. | 257/419 |
| 5,414,284 A * | 5/1995 | Baxter et al. | 257/253 |
| 5,607,566 A | 3/1997 | Brown et al. | |
| 5,918,110 A | 6/1999 | Abraham-Fuchs et al. | |
| 6,111,280 A * | 8/2000 | Gardner et al. | 257/253 |
| 6,117,643 A | 9/2000 | Simpson et al. | |
| 6,215,155 B1 | 4/2001 | Wolleson | |
| 6,294,133 B1 * | 9/2001 | Sawada et al. | 422/82.01 |
| 6,326,288 B1 | 12/2001 | Bornefeld | |
| 6,387,724 B1 | 5/2002 | Walker | |
| 6,388,279 B1 * | 5/2002 | Sakai et al. | 257/254 |
| 6,429,502 B1 * | 8/2002 | Librizzi et al. | 257/510 |
| 6,661,096 B1 | 12/2003 | Takayama et al. | |
| 6,673,596 B1 | 1/2004 | Sayler et al. | |
| 6,747,339 B1 | 6/2004 | Mukai et al. | |
| 6,768,174 B2 | 7/2004 | Hasegawa et al. | |
| 6,798,184 B2 | 9/2004 | Honda | |
| 2001/0025963 A1 | 10/2001 | Tashiro et al. | |
| 2002/0038890 A1 | 4/2002 | Ohuchi | |
| 2002/0063304 A1 | 5/2002 | Toeda et al. | |
| 2002/0110989 A1 | 8/2002 | Yamaguchi et al. | |
| 2003/0001280 A1 | 1/2003 | Noguchi et al. | |
| 2003/0102872 A1 | 6/2003 | Honda | |
| 2004/0077116 A1 | 4/2004 | Hsiung et al. | |
| 2004/0121354 A1 | 6/2004 | Yazawa et al. | |
| 2004/0150070 A1 * | 8/2004 | Okada et al. | 257/508 |
| 2005/0067618 A1 | 3/2005 | Nakajima et al. | |
| 2005/0285155 A1 * | 12/2005 | Johnson et al. | 257/253 |

FOREIGN PATENT DOCUMENTS

| | | |
|---|---|---|
| DE | 4430811 C1 | 8/1994 |
| EP | 0 999 595 A2 | 11/1999 |
| EP | 1 168 430 A1 | 12/2000 |
| GB | 2 321 336 A | 1/1997 |
| JP | 62024659 | 7/1985 |
| JP | 63-195557 | 2/1987 |
| JP | 3-33646 | 6/1989 |
| JP | 3122558 | 10/1989 |
| JP | 3249557 | 2/1990 |
| JP | 6-177233 | 12/1992 |
| JP | 6-177242 | 12/1992 |
| JP | 6177242 | 12/1992 |
| JP | 9-210955 | 1/1996 |
| JP | 9210955 | 1/1996 |
| JP | 11126819 | 6/1998 |
| JP | 2002-014072 | 6/2000 |
| JP | 2003-78142 | 9/2001 |
| JP | 2003-158198 | 8/2002 |
| WO | WO 87/03687 | 6/1987 |
| WO | WO 94/22006 | 2/1994 |

OTHER PUBLICATIONS

Chin, Y.L. et al., "A Novel $SnO_2/Al$ Discrete Gate ISFET pH Sensor with CMOS Standard Process", Sensors and Actuators, B75, 2001, XP-001150294, pp. 36-42.

Wong, H.S et al., "A CMOS-Integrated 'ISFET-Operational Amplifier' Chemical Sensor Employing Differential Sensing", IEEE Transactions on Electron Devices, vol. 36, No. 3, Mar. 1989, XP000036564, pp. 479-487.

Partial European Search Report for 04021003.1.-1235 dated Feb. 21, 2008.

Van Der Spiegel et al., "The Extended Gate Chemically Sensitive Field Effect Transistor As Multi-Species Microprobe", Sensors and Actuators, 4 (1983) pp. 291-298.

Tsukada, K. et al., "An Integrated Micro Multi-Ion Sensor Using Platinum-Gate Field-Effect Transistors", IEEE, (1991), pp. 218-221.

Extended European Search Report dated Aug. 18, 2008 regarding European Application No. 08007071.7-1235/1950808.

* cited by examiner

FIG. 14 ssDNA—( primer + (dNMP)$_n$ ) + dNTP $\xrightarrow{\text{polymerase}}$ ssDNA—( primer + (dNMP)$_{n+1}$ ) + PPi PPi + APS $\xrightarrow{\text{ATP sulfuryrase}}$ ATP + SO$_4^{2-}$ luciferin + ATP + O$_2$ $\xrightarrow{\text{luciferase}}$ AMP + PPi + oxyluciferin + CO$_2$ + h$\nu$

EXAMINATION APPARATUS FOR BIOLOGICAL SAMPLE AND CHEMICAL SAMPLE

CROSS-REFERENCE TO RELATED APPLICATION

This application is a Divisional of U.S. application Ser. No. 10/933,339 filed Sep. 3, 2004 now abandoned, which claims the priority of Japanese Patent Application No. 2004-012596 filed Jan. 21, 2004. Priority is claimed based U.S. application Ser. No. 10/933,339 filed Sep. 3, 2004, which claims the priority of Japanese Patent Application No. 2004-012596 filed Jan. 21, 2004, all of which is incorporated by reference.

TECHNICAL FIELD OF THE INVENTION

The present invention relates to a sensor and a system, in which the sensor is put into or comes into contact with a sample and results thereof are transmitted wirelessly to an external device. As the examples of the system mentioned above, a system for detecting biological materials such as nucleic acid, protein, antigen, and antibody and a system for measuring physical and chemical quantity such as temperature, pressure, light, and ion concentration can be shown.

BACKGROUND OF THE INVENTION

Japanese Patent Laid-Open Application No. 2002-14072 discloses an integrated circuit device called an integrated sensor device, in which a sensor portion, a control unit for processing the signals representing the detection results of the sensor portion, and an antenna for receiving the energy required for the communication with outside and the circuit operation from outside are integrated on one chip. It also discloses that an ion sensitive field effect transistor (hereinafter, referred to as ISFET) and an organic film whose characteristics are changed when it contacts to gas or liquid containing a substance are used as the sensor portion of this integrated sensor device.

An extended gate structure disclosed in J. van der Spiegel, I. Lauks, P. Chan, D. Babic, "The extended gate chemically-sensitive field effective transistor as multi species microprobe, Sensors and Actuators" 4 (1983) pp. 291-298, and K. Tsukada, Y. Miyahara, Y. Shibata, H. Miyagi, "An integrated micro multi-ion sensor using platinum-gate field effect transistors", Proc. Int. Conf. Solid-State Sensors and Actuators (Transducers '91), San Francisco, USA, 1991, pp. 218-221 is known as a structure suitable for the monolithic integration of the ISFET with the integrated circuit.

Also, the problem that the device characteristics and the electric insulation between devices are degraded due to the penetration of positive ions into the device forming region in a semiconductor integrated circuit device with the SOI structure is examined in Japanese Patent Laid-Open Application No. 6-177233, Japanese Patent Laid-Open Application No. 6-177242.

SUMMARY OF THE INVENTION

Starting with the gene test and the protein test, the system capable of easily measuring biological and chemical materials has been demanded in various fields. In order to meet such demands, the inventors of the present invention examine the wireless sensor chip (hereinafter, referred to as sensor chip) in which a sensor for measuring a biological material such as DNA, a chemical material, ion, and physical quantity and a mechanism for wirelessly transmitting the sensing data to the outside of a chip are integrated on a semiconductor chip. Japanese Patent Laid-Open Application No. 2002-14072 does not describe what type of device the integrated sensor device can be. Especially, it is desired that the device can be manufactured simply by the current semiconductor manufacturing process so as to realize the measurement system at low cost.

Also, it is also necessary that the device can maintain its reliability even when the sensor chip is used in a solution.

The method for solving the above-described problems is shown below.

A sensor chip is formed on an SOI substrate. However, the n type semiconductor region in which the PMOS transistor is formed and the p type semiconductor region in which the NMOS transistor is formed are isolated from each other by the pn junction. This can be achieved by applying the minimum potential of the sensor chip as the substrate potential of the p type semiconductor region and applying the maximum potential of the sensor chip as the substrate potential of the n type semiconductor region.

Also, the integrated circuit constituting the sensor chip is surrounded by an n type (p type) semiconductor region (guard ring) which reaches the buried insulating layer of the SOI substrate, and its outer periphery is made to be a p type (n type) semiconductor region. In addition, the maximum potential (minimum potential) of the sensor chip is applied to the guard ring, and the semiconductor region of its outer periphery is set to floating.

Furthermore, in order to prevent the penetration of positive ions through the oxide layer, the chip is covered with an ion impermeable insulating film.

It is possible to provide a sensor chip suitable for the detection of a biological material such as gene and a chemical material and the measurement of physical-chemical quantity such as temperature, pressure, and pH.

BRIEF DESCRIPTIONS OF THE DRAWINGS

FIG. 14 shows chemical equations of the complementary strand extension of primer.

DESCRIPTIONS OF THE PREFERRED EMBODIMENTS

Hereinafter, embodiments of the present invention will be described in detail with reference to the accompanying drawings. Note that components having the same function are denoted by the same reference symbols throughout the drawings for describing the embodiments, and the repetitive description thereof will be omitted.

Figure 2:
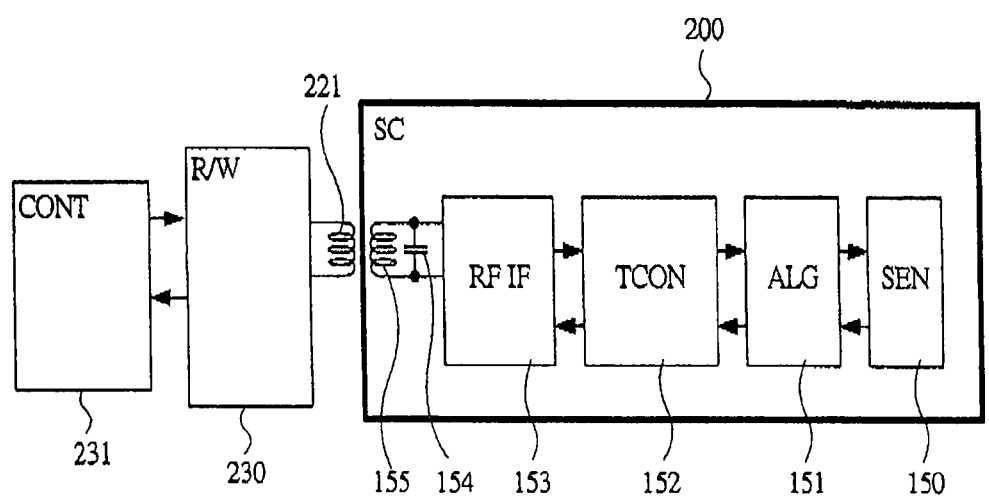
FIG. 2 is a block diagram showing the configuration of the wireless sensing system using the sensor chip.

FIG. 2 shows an example of the measurement system using the sensor chip. First, a sensor chip 200 will be described. A sensor block 150 is comprised of a sensor such as an ISFET, a thermometer, and a photodiode. It is also possible to use a plurality of sensors or several types of sensors to form the sensor block 150. A sensor analog block 151 includes a signal processing circuit such as an amplifier for amplifying sensing signals from the sensor block 150 and an A/D converter for converting amplified sensing signals to digital signals and a sensor control circuit for controlling the sensor block 150. A communication control circuit block 152 controls the communication between the sensor chip 200 and a reader/writer 230. An RF interface block 153 includes a receiver circuit for receiving signals from the reader/writer 230, a transmitter circuit for transmitting sensing data, and a rectifier for generating power and clock. The RF interface block 153 is connected to a coil 155 and a resonant capacitor 154 performing the data communication and the power transmission.

After the sensing data is converted to the digital signal in the sensor analog block 151, it is converted to the radio frequency signal in the RF interface block 153 and is transmitted to the reader/writer 230 through an RF carrier wave. Also, the power consumed in the circuit blocks 150 to 153 mounted on the sensor chip is supplied by the inductive coupling of the reader/writer 230 and an antenna 221.

A measurement control device 231 controls the reader/writer 230 and collects the sensing data by using the sensor chip 200, and also, it processes the sensing data.

Figure 3A:
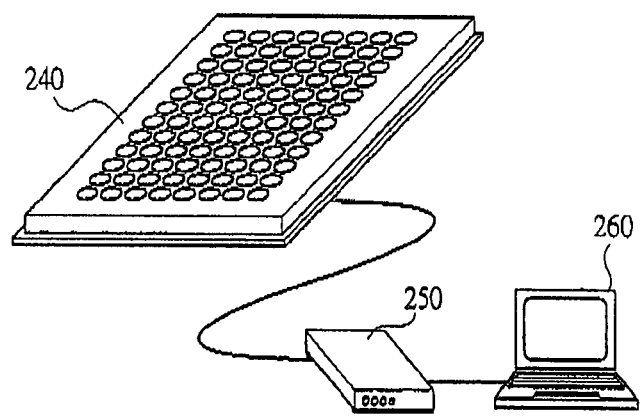
FIG. 3A is a diagram showing an example of the usage of the sensor chip.
Figure 3B:
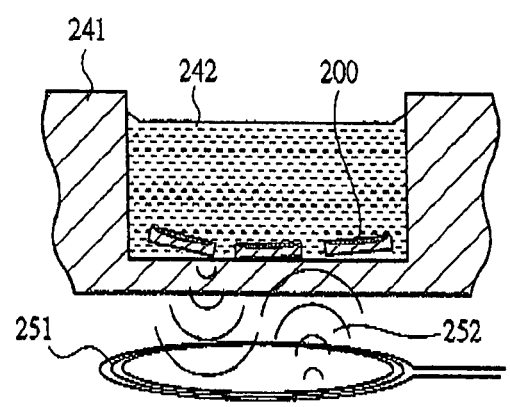
FIG. 3B is an enlarged diagram of a reaction vessel of FIG. 3A.

FIGS. 3A and 3B show an example of the chip usage in the measurement system using the sensor chip. FIGS. 3A and 3B show an example of the chip usage for obtaining the sensing data with the sensor chips being put into a solution. As shown in FIG. 3A, a computer 260 is used as the measurement control device 231, and the sensing data is collected from the sensor chips 200 through the data/writer 230. A plurality of reaction vessels 241 are provided in a plate 240. FIG. 3B is an enlarged diagram of the reaction vessel 241. The sensor chips 200 are put into the reaction vessel 241 filled with sample solution 242, and the reader/writer side coil 251 provided outside the reaction vessel 241 supplies power and transmits control signals to the sensor chips 200 and receives sensing data from the sensor chips 200. Any of the electromagnetic wave, change in magnetic field, and change in electric field can be used for the communication between the sensor chip 200 and the reader/writer 230.

Figure 4:
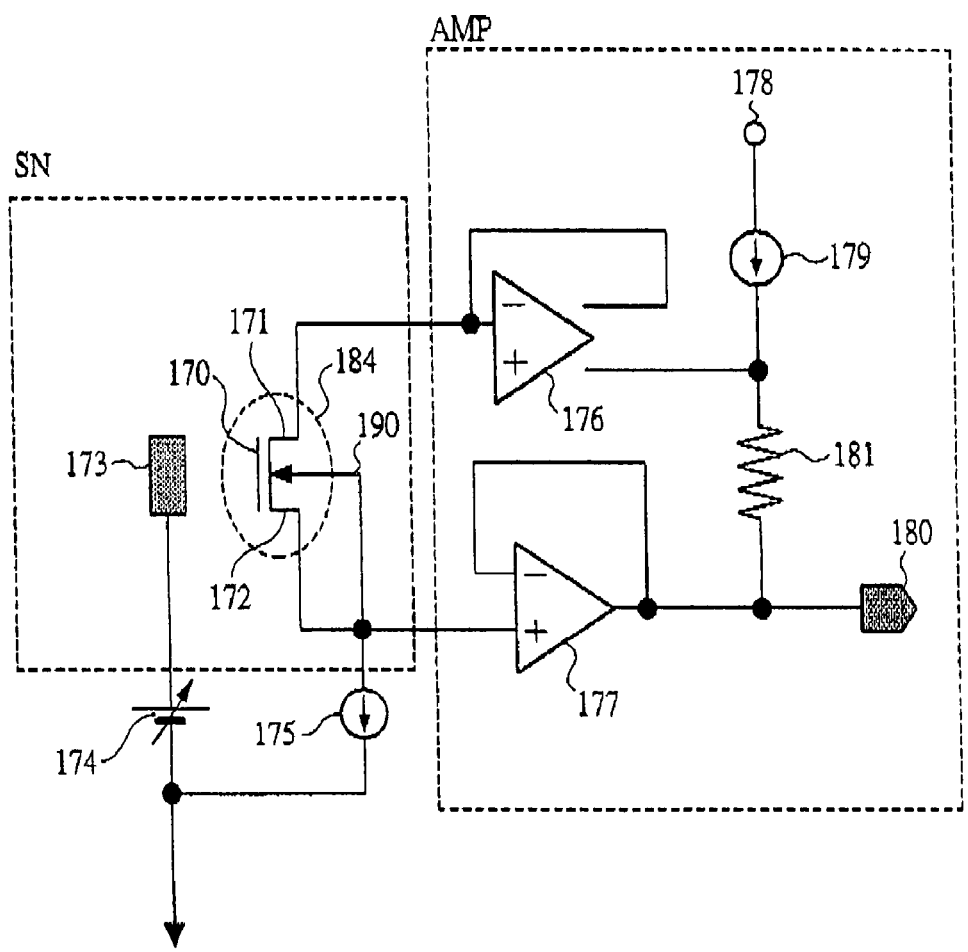
FIG. 4 is a block diagram showing the configuration of the sensor circuit using the ISFET as the sensor of the sensor chip.

Hereinafter, an example of a sensor chip using an ISFET as a sensor will be described. FIG. 4 is a diagram showing an example of a circuit configuration provided with a sensor SN included in the sensor block 150, an amplifier AMP included in the sensor analog block 151, a bias circuit 174, and a constant current source 175. In this measurement, an ion sensitive film 170 and a reference electrode 173 provided on the gate of the ISFET 184 are put into contact with the sample solution 242. The description will be made with taking a pH sensor as an example. For example, an $Si_3N_4$ film (silicon nitride film) can be used as the ion sensitive film 170 in order to make the sensor function as the pH sensor. The $Si_3N_4$ film is bonded with hydrogen ion ($H^+$) in the sample solution. When an amount of hydrogen ions depending on the hydrogen ion concentration of the sample solution is bonded to the $Si_3N_4$ film, it reaches the equilibrium. Meanwhile, the potential of the reference electrode 173 is applied as the reference potential of the source potential (substrate potential) of the ISFET 184. The ideal reference electrode has such characteristics that the potential distribution at the interface between the electrode and the solution is not varied regardless of kinds and concentration of the solution. When the concentration of the hydrogen ions is high relative to the stable source potential, the amount of hydrogen ions to be bonded to the $Si_3N_4$ film is increased and the channel resistance of the ISFET 184 is reduced. On the other hand, when the concentration of the hydrogen ions is low, the amount of hydrogen ions to be bonded to the $Si_3N_4$ film is also reduced and the channel resistance of the ISFET 184 is increased. Therefore, the hydrogen ion concentration of the sample solution can be measured by detecting the change described above.

The constant current source 175 and the amplifier circuit AMP are provided in order to detect the above-described change. The drain voltage Vds of the ISFET 184 is controlled so as to be constant voltage given by the constant current source 179 and the resistance 181. Also, since a constant current source 175 and the ISFET 184 are connected in series, the drain current Ids of the ISFET 184 is constant current. The difference between the channel resistance depending on the hydrogen ion concentration and Vds/Ids is detected as the change of the potential of a node N1. The hydrogen ion concentration of the sample solution is measured by reading the potential of the node N1 from an output terminal 180 via a voltage follower amplifier 177.

Figure 6:
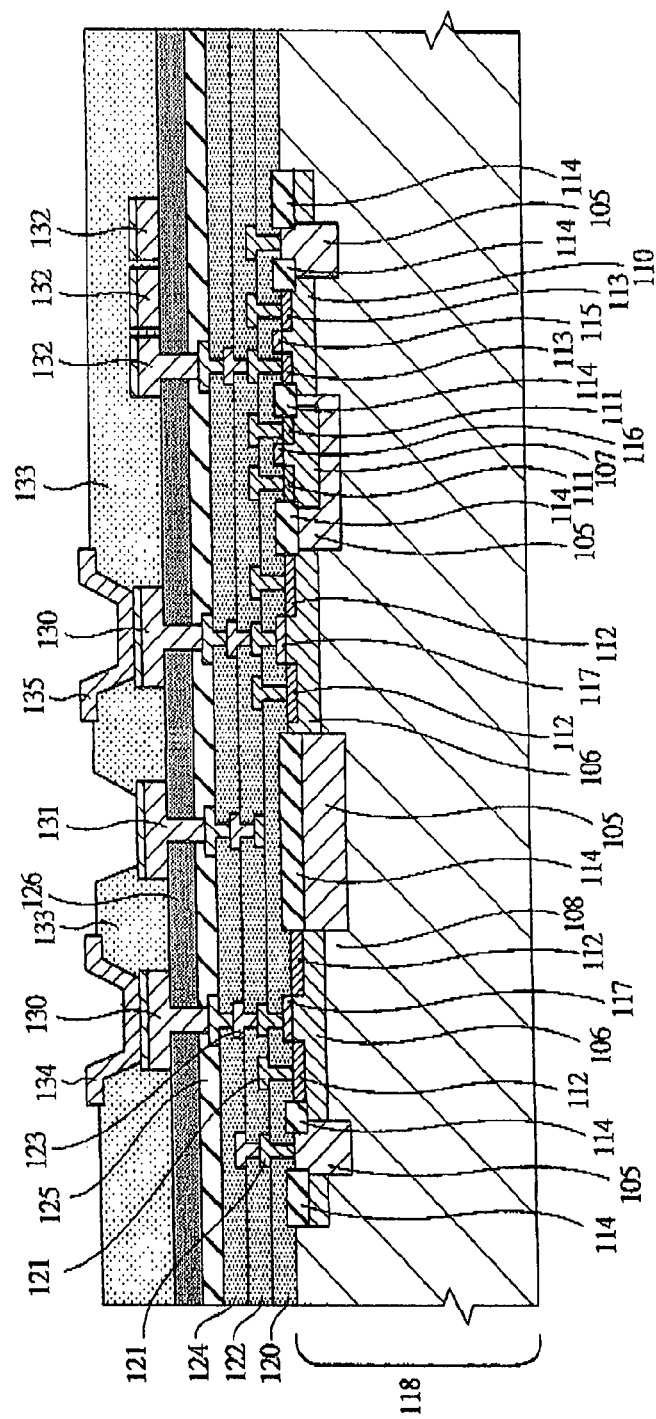
FIG. 6 is a cross-sectional view showing the structure assumed when the sensor chip is formed by the bulk CMOS process.

Note that the bias circuit 174 supplies a predetermined bias potential to the potential of the reference electrode 173 in order to enhance the detection sensitivity by the ISFET 184. Also, in order to reduce the power consumption of the sensor chip, the power supply of the constant current source 174 and the bias circuit 174 is stopped by a sensor control circuit (not shown) when the sensor is not operated. Also, in FIG. 4, the reference character 171 denotes a drain of the ISFET, 172 denotes a source of the ISFET, 176 denotes an amplifier, and 178 denotes a power source In order to detect the potential of the node N1 by using the circuit shown in FIG. 4, it is necessary that the high impedance exists between the node N1 and the node N2. Meanwhile, in order to form the device at low cost, the device is preferably composed of bulk CMOS. It is assumed that the sensor chip is composed of standard bulk CMOS for the comparison with the sensor chip of this embodiment. FIG. 6 is a cross-sectional view of the sensor chip composed of bulk CMOS. The detailed description thereof will be omitted here. However, since the node N1 is a well 106 and the high impedance exists between the node N1 and the node N2, this well is set to floating. Since the sensor chip is not resin-sealed, that is, used as a so-called bare chip for the cost reduction, an electrode 131 corresponding to the reference electrode 173 and a substrate 118 are short-circuited by the sample solution. Therefore, the inventor found out that the sensor chip simply composed of standard bulk CMOS cannot maintain the high impedance between the node N1 and the node N2. As described above, it is necessary to prevent the short circuit between an electrode and a semiconductor region via a sample solution in the case of the sensor chip to be used in the sample solution.

Figure 1:
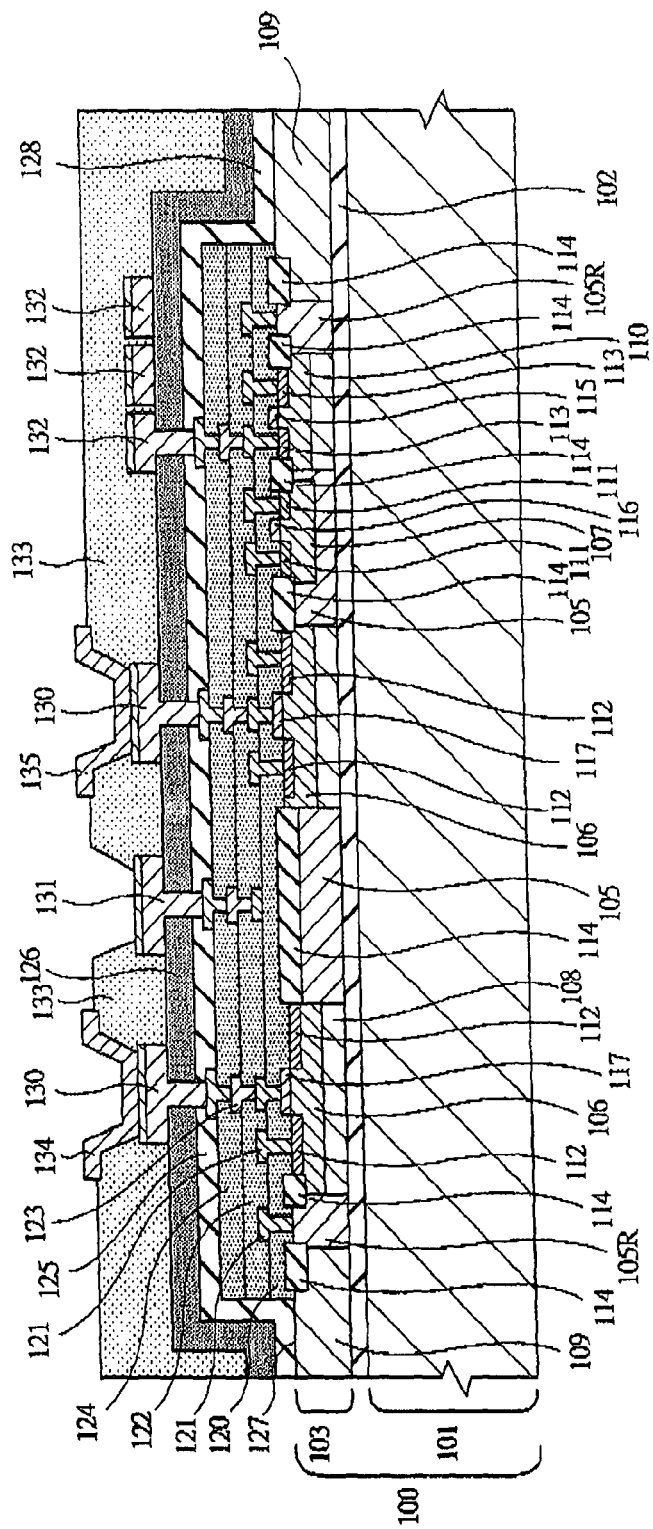
FIG. 1 is a cross-sectional view showing the structure of the sensor chip according to the present invention.

FIG. 1 shows a sectional structure of the sensor chip of the present invention. An ISFET is used as a sensor and the sensor (ISFET) and a wireless communication device are formed on the same semiconductor substrate as described in FIG. 2. The sensor chip includes two ISFETs, and the first ISFET has an ion selection film 134 for selectively taking the target ions and the second ISFET has an ion selection film 135 for selectively taking the target ions different from those taken by the first ISFET. Due to the difference in ion selectivity, the amount of ions taken from the sample solution into the films differs between the first ISFET and the second ISFET, and the potential of the gates in respective ISFETs differs from each other. By measuring this as the difference in the channel conductance (resistance) of the ISFETs, the ion concentration of the sample solution can be obtained. The advantage of this structure will be described later with reference to FIG. 10.

It is desired that the change for the standard CMOS process is reduced to minimum so as to achieve the cost reduction and the structure with high reliability capable of electrically isolating the substrate from the sample solution can be obtained. Therefore, an SOI (Silicon on Insulator) substrate is used as the semiconductor substrate to realize the electric isolation of the chip rear surface. In addition, with respect to the edge of the chip, a guard ring as an impurity diffusion layer which reaches the buried insulating layer (buried oxide layer: hereinafter, referred to as BOX layer) of the SOI substrate is formed on the periphery of the chip, and a p type or n type impurity diffusion layer is formed inside the guard ring. Also, the impurity diffusion layer on the outer periphery of the guard ring is set to floating potential and the potential of the impurity diffusion layer inside the guard ring is set to the reverse bias potential relative to the potential of the impurity diffusion layer of different conductivity type. By doing so, the insulation structure by the pn junction can be obtained.

Also, the reduction of the penetration of positive ions through the exposed portion of the oxide film is also important for the enhancement of the device reliability. When an exposed portion of the oxide film is present on the edge of the chip, positive ions such as sodium penetrate. For example, in the structure shown in FIG. 6, the positive ions penetrate through the interlayer insulating film 120, 122, or 124 made of silicon oxide ($SiO_2$) exposed at the edge and cause the degradation of characteristics of the device formed on the semiconductor substrate 118 such as the threshold voltage of the MOS transistor and the leakage characteristics of the pn junction. Since it is assumed that the sensor chip is used as an unpackaged chip in order to achieve the cost reduction, it is necessary to prevent the penetration of positive ions in the chip level.

As described above, in order to satisfy the requirement to use the unpackaged chip in a solution, the following two conditions are important for the enhancement of the reliability of a sensor chip. That is, the first is to insulate the rear surface and the edge of the chip from the solution, and the second is to prevent the penetration of positive ions through the edge of the chip.

As shown in FIG. 1, the sensor and each circuit block are formed on the SOI substrate 100. On the SOI substrate, a single crystal silicon layer (p type, 10 Ωcm) with a thickness of 2 μm is formed on the BOX layer. The NMOS transistor (the term "MOS transistor" is used as a generic term of an insulating-gate field effect transistor) is formed in the p type well 110 and the pMOS transistor is formed in the n type well 107. These MOS transistors are transistors used in the circuit blocks 151 to 153 in FIG. 2. Also, the ISFET constituting the sensor has the same gate structure as that of the NMOS transistor. The potential of the gate 117 of the ISFET is set to floating and is connected to the ion sensitive film 134 or the reference ion sensitive film 135 via the wiring layers 121, 123, and 130. The structure of the ISFET described above suitable for the multilayer wiring structure is called an extended gate structure (see, Japanese Patent Laid-Open Application No. 2002-14072 and Japanese Patent Laid-Open Application No. 6-177233), and it has an advantage the standard process for forming a MOS transistor can be used with almost no change. Of course, the structure in which the ion sensitive films 134 and 135 are arranged directly on the gate 117 can be used as the structure of the ISFET. Note that, in, FIG. 1, the reference character 115 denotes a gate of an n-channel MOS transistor, and 116 denotes a gate of a p-channel MOS transistor.

The adjacent nMOS are isolated from each other by a field insulating film 114. In the example shown in FIG. 1, the field insulating film has a thickness not reaching the BOX layer, for example, 450 nm. As described above, the MOS transistors of the same conductivity type are isolated by a field insulating film. Furthermore, the MOS transistors of different conductivity types are isolated by a field insulating film and by setting the potentials of the n well and p well in which each of the MOS transistors is formed so as to reversely bias the pn junction. At this time, when it is assumed that the thickness of the field insulating film is 450 nm, the thickness of the field insulating film below the main surface of the silicon substrate is 200 nm and the thickness of the field insulating film above the main surface of the silicon substrate is 250 nm. Since the depth of the well diffusion layer is about 1000 nm, the well diffusion layer is provided below the field insulating film and a plurality of MOS transistors are formed in the same well.

A first wiring layer 121 and a second wiring layer 123 are formed after forming the MOS transistors. Next, an ion impermeable insulating film 125 is deposited on an oxide insulating film 124. At this time, the oxide insulating films 120, 122, and 124 in the chip peripheral portion are removed to expose the silicon layer 109 before depositing the ion impermeable insulating film 125. Then, by depositing the ion impermeable insulating film 125, the ion impermeable insulating film 125 and the silicon layer 109 come into contact with each other at silicon layer exposed portions 127 and 128 in the chip peripheral portion, and the diffusion path of the positive ions of the oxide insulating films 120, 122, and 124 is shut.

Phosphosilicate glass (PSG) or silicon nitride ($Si_3N_4$) can be used as the ion impermeable insulating film 125. The PSG has a function to capture the positive ions diffused into the oxide insulating film by using phosphorus. In the example of FIG. 1, a silicon nitride film with a thickness of 150 nm is used as the material scarcely permeating ions. The silicon nitride has an advantage that it is superior in water resistance in comparison to PSG.

After forming the ion impermeable insulating film 125, an insulating film 126 is deposited and a metal layer for forming a connection portion 130 to the ion sensitive films 134 and 135, a coil 132, and a pseudo reference electrode 131 is formed. Copper of 10 μm is used as the metal layer. The pseudo reference electrode is an electrode for applying a reference potential to the gate of the ISFET with reference to the solution potential when sensor chips are put into the solution (reference electrode 173 in FIG. 4). Although the potential distribution at the interface between an electrode and a solution is not varied due to the kinds and the concentration of the solution in the case of the ideal reference electrode, a normal hydrogen electrode or an Ag—AgCl electrode approximately satisfying the condition is used as the electrode in practice. However, these electrodes are not suitable from the viewpoint of the compatibility with the process of forming the semiconductor integrated circuit. Therefore, a material at least chemically stable to the solution is used for the reference electrode though it does not completely satisfy the condition that the potential distribution at the interface between the electrode and the solution is not varied (for this reason, that is, because it is not an ideal reference electrode, the term of "pseudo" reference electrode is used.).

Figure 5A:
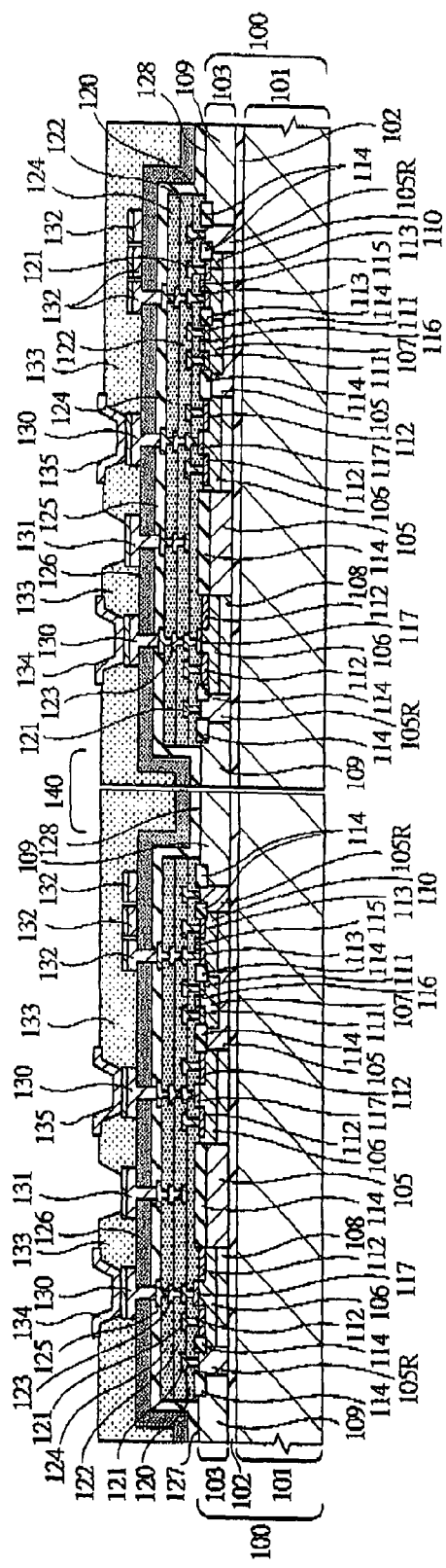
FIG. 5A is a cross-sectional view of the sensor chip in the wafer level.
Figure 5B:
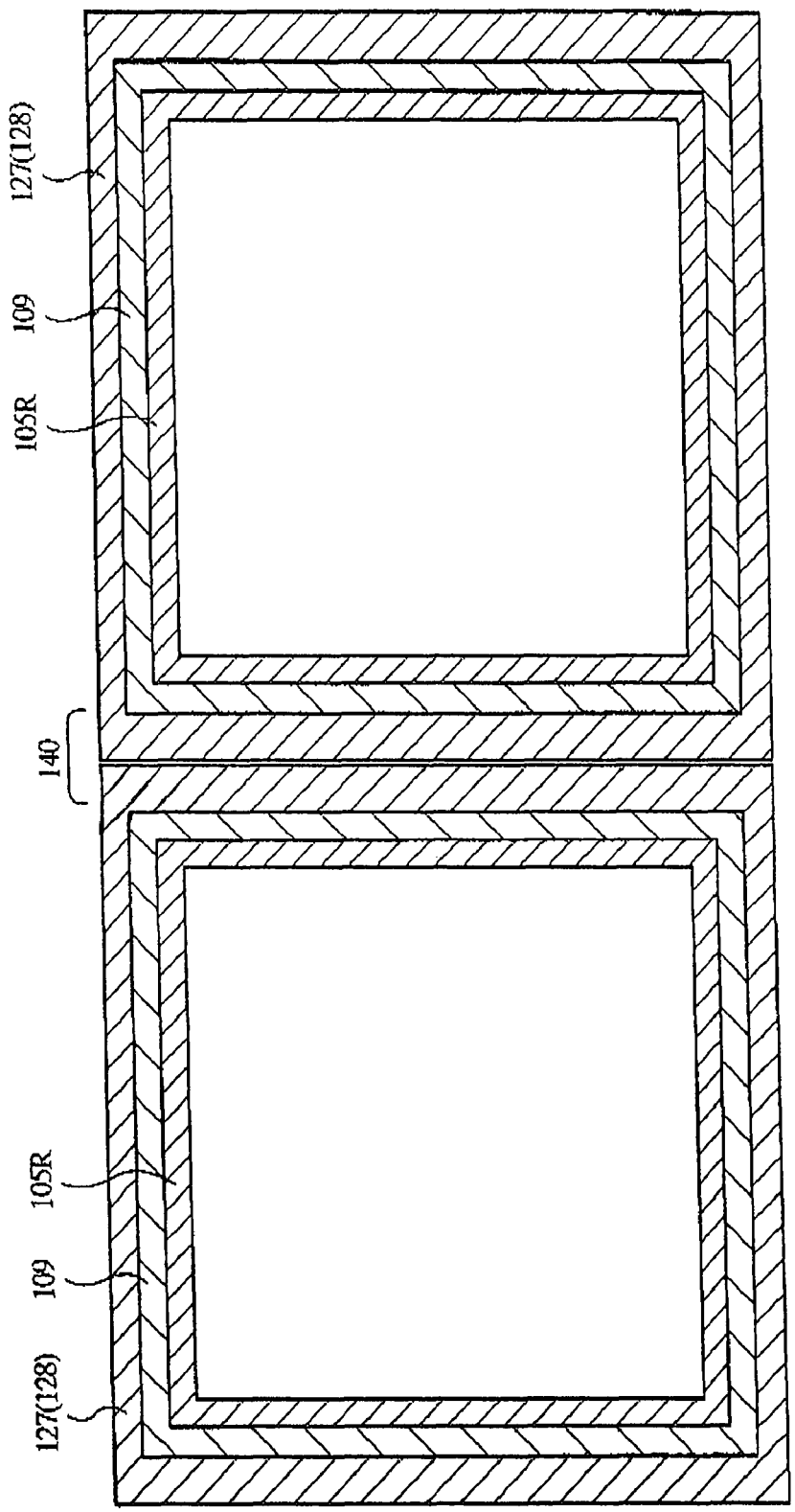
FIG. 5B is a plan view of the sensor chip in the wafer level.

For example, gold with a thickness of 100 nm is formed after forming an adhesive metal layer to copper. Before forming metal layers 130, 131, and 132, the insulating layers 123, 125, and 126 are processed to form through holes, and the necessary connection to the integrated circuit portion is made. After forming the metal layers 130, 131, and 132, an insulating film 133 is deposited and a through hole is formed in a part of the gate connection electrode 130 of the ISFET. Then, the ion sensitive films 134 and 135 connected to the gates of the first ISFET and the second ISFET are formed, respectively. FIGS. 5A and 5B show the state where the chips shown in FIG. 1 are formed on a wafer (the area including two chips is illustrated). FIG. 5A is a cross-sectional view and FIG. 5B is a plan view. However, FIG. 5B shows the layout of the several layers (semiconductor regions) that cannot see in the completed product. A region 105R is the guard ring, a region 109 is a outer peripheral region of the guard ring, and contact regions 127 and 128 between the ion impermeable insulating film 125 and the region 109 are present on the region 109. After forming the integrated circuit, the sensor, the coil, and the ion sensitive film to complete the wafer, it is diced at the scribe region (separation region) 140 into respective chips.

The electric isolation of the sensor chip will be described based on the sensor chip shown in FIG. 1 and FIGS. 5A and 5B. The electric isolation on the chip rear surface is achieved by the BOX layer 102. Also, the electric isolation on the chip side surface can be achieved by the structure described below. That is, it can be achieved by the structure in which the conductivity type of the silicon layer 103 is made to be p type, a p type impurity diffusion layer 109 is arranged around the chip, and an n type impurity diffusion layer 105R (guard ring) which reaches the BOX layer 102 is arranged inside the p type impurity diffusion layer 109. The n type impurity layer 105 is formed as a diffusion layer formed under the ion implantation and diffusion conditions that make it possible to have the diffusion depth which reaches the BOX layer 102. As shown in FIG. 5B, the guard ring 105R is arranged along the chip periphery and is connected to the maximum potential in the chip. The p type impurity diffusion layer 109 on the outer periphery thereof is set to electrically floating. The p type substrate 108 inside the guard ring 105R and the p type well 110 of the nMOS transistor are set to the ground potential of the chip, and the n type well 107 of the PMOS transistor and the deep n type impurity diffusion region 105 are set to the maximum potential of the chip. The power supply voltage used in the integrated circuit is used as the maximum potential of the chip, for example, it is set to 3V.

Therefore, even when the potential of the p type floating layer 109 is increased by the potential of the sample solution, since the guard ring layer 105R and the floating layer 109 are reversely biased, the insulation between the sensor chip and the solution can be maintained as far as within the power supply voltage. Also, the ground potential of the chip differs by only the bias potential 174 on the basis of the pseudo reference electrode 173. When the bias potential generated in the integrated circuit of the chip is set lower than the power supply potential, the insulation of the integrated circuit is not lost. Note that, for setting the floating layer 109 to n type, the guard ring is set to p type and the ground potential of the chip is set thereto.

Also, the polarity of the impurity diffusion layer is not limited to the description above. For example, even in the case where the sensor chip is formed on the n type SOI substrate, the same effects can be obtained by giving the suitable polarity of a diffusion layer and well potential.

Next, the reduction of diffusion of the positive ions from the chip edge will be described. First, the diffusion path of the positive ions will be described. In the portion above the main surface of the SOI substrate 100, the diffusion path of the positive ions through the oxide insulating film from the chip edge portion is shut by the ion impermeable film 127. In addition, the BOX layer 102 can be cited as a silicon oxide film formed below the main surface of the SOI substrate, and the BOX layer 102 can be the diffusion path of the positive ions. As described in the structure of FIG. 1, since the thickness of the field insulating film 114 which isolates the devices is smaller than that of the silicon layer 103, the field insulating film 114 does not reach the BOX layer 102. Therefore, the BOX layer 102 is isolated from the oxide layer formed above the main surface of the SOI substrate 100, and thus, the positive ions diffused through the BOX layer 102 into the substrate do not reach the devices constituting the integrated circuit formed on the main surface of the substrate. Also, as the region which may be influenced by the positive ions diffused into the BOX layer, there are the p type well 110 of the nMOS transistor, the n type well 107 in which the PMOS transistor is formed, and the deep n type isolation layer 105 for isolating the p type well layer. However, in these regions, the p type well is fixed to the minimum potential, and the n type well and the deep n type isolation layer are fixed to the maximum potential as described above. Therefore, the influence of the positive ions in the BOX layer does not reach the channel region of the MOS transistor which operates the integrated circuit and the region of the n/p type diffusion layers which constitute the source and drain, and the diffusion layer resistor.

As described above, the structure of the MOS transistor and the ISFET shown in FIGS. 1 and 5 is identical to that not using the SOI substrate, and the structure unique to the SOI substrate is unnecessary. Therefore, it can be manufactured through the usual process for the general-purpose substrate. In addition, with respect to the layout, it is not necessary to fix the well potential in each MOS transistor, and similar to the bulk CMOS, it is preferable that the contact portion to the wiring for setting the potential is provided at any optional parts in the common well including a plurality of MOS transistors. Furthermore, with respect to the device isolation and the setting of the well potential, it is possible to design the integrated circuit based on the layout rule similar to that of the normal silicon substrate without the SOI structure. Consequently, since it is possible to use the process for the general-purpose transistor and the conventional circuit design data, the highly stable and reliable sensor chip excellent in chip insulation characteristics can be provided at low cost and in a short amount of time.

Figure 7:
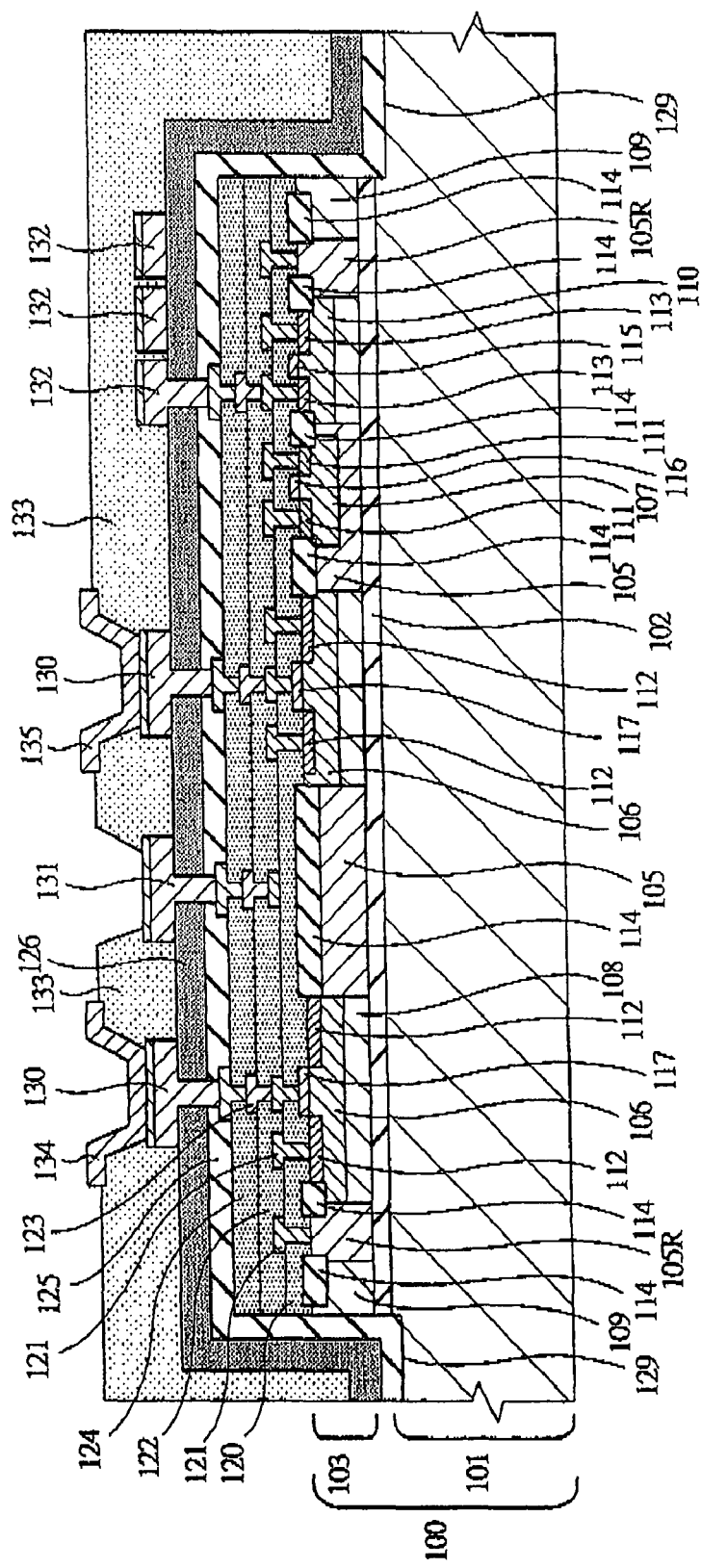
FIG. 7 is a cross-sectional view showing another structure of the sensor chip according to the present invention.

FIG. 7 is a cross-sectional view showing the first modified example of the device structure of the sensor chip. The difference from the structure in FIG. 1 is that the trench deeper than the BOX layer 102 is formed in the peripheral portion of the chip before the deposition of the ion impermeable insulating film 125, and the ion impermeable insulating film 125 is deposited thereon. By doing so, the ion impermeable insulating film 125 directly contacts to the SOI support substrate 101. Therefore, the electric isolation of the chip edge can be achieved by the ion impermeable insulating film 125, and also, the diffusion path of the positive ions is shut by the ion impermeable insulating film 125. The characteristics of this structure is that the BOX layer 102 is also separated from the chip edge. Therefore, it is possible to reduce the diffusion of positive ions into the chip through the chip edge. Hence, when this structure is used, the influence of the positive ions diffused into the BOX layer 102 can be prevented even in the structure shown in FIG. 4 in which the potential of the well 190 varies.

Figure 8:
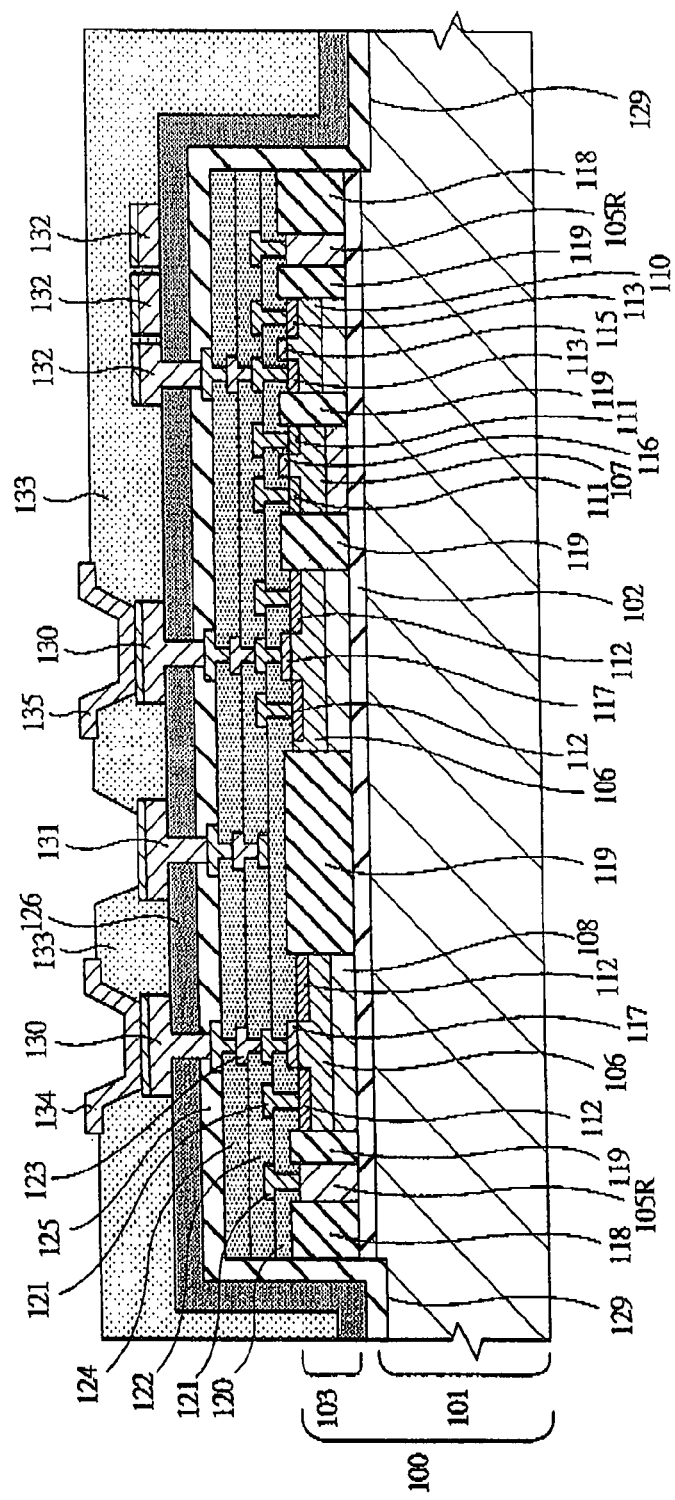
FIG. 8 is a cross-sectional view showing another structure of the sensor chip according to the present invention.

FIG. 8 is a cross-sectional view showing the second modified example of the device structure of the sensor chip. The difference from the structure in FIG. 1 is that the thickness of the field insulating film 119 is made equal to or larger than that of the silicon film on the BOX. By doing so, the MOS transistor is isolated by the insulating film, and hence, it is possible to improve the breakdown voltage of the device isolation and the breakdown voltage of the latch-up between MOS transistors. However, if the positive ions are diffused from the BOX layer 102 in this structure, the device characteristics are adversely affected. Therefore, the structure similar to that of FIG. 7 is used as the structure around the chip. More specifically, since the portion around the chip is isolated by the ion impermeable insulating film 125, the problem of the diffusion of positive ions does not occur.

In this modified example, the structure in which the field insulating films 118 and 119 reach the BOX layer is used, and such a structure can be achieved in the following manner. That is, (1) the silicon layer 103 on the BOX layer 102 is made thinner. For example, the thickness of the silicon layer 103 is set to 150 nm and that of the field insulating film is set to 450 nm (the thickness below the main surface of the SOI substrate is set to 200 nm). (2) The thickness of the silicon layer 103 is set to 2 μm and a deep trench is formed in the device isolation region and an insulating film is deposited thereon. (3) The thickness of the silicon layer 103 is set to 500 nm and that of the field insulating film is set to 1.5 μm. For example, when the method of (1) is used, the source and drain regions 111, 112, and 113 of the MOS transistor come into contact with the BOX layer 102. Therefore, it becomes possible to reduce the parasitic capacitance between the source and drain regions and the silicon layer or that between the wiring on the field insulating film and the silicon layer, and thus, the reduction of power consumption and the increase of the operation speed of the integrated circuit can be achieved.

Figure 9:
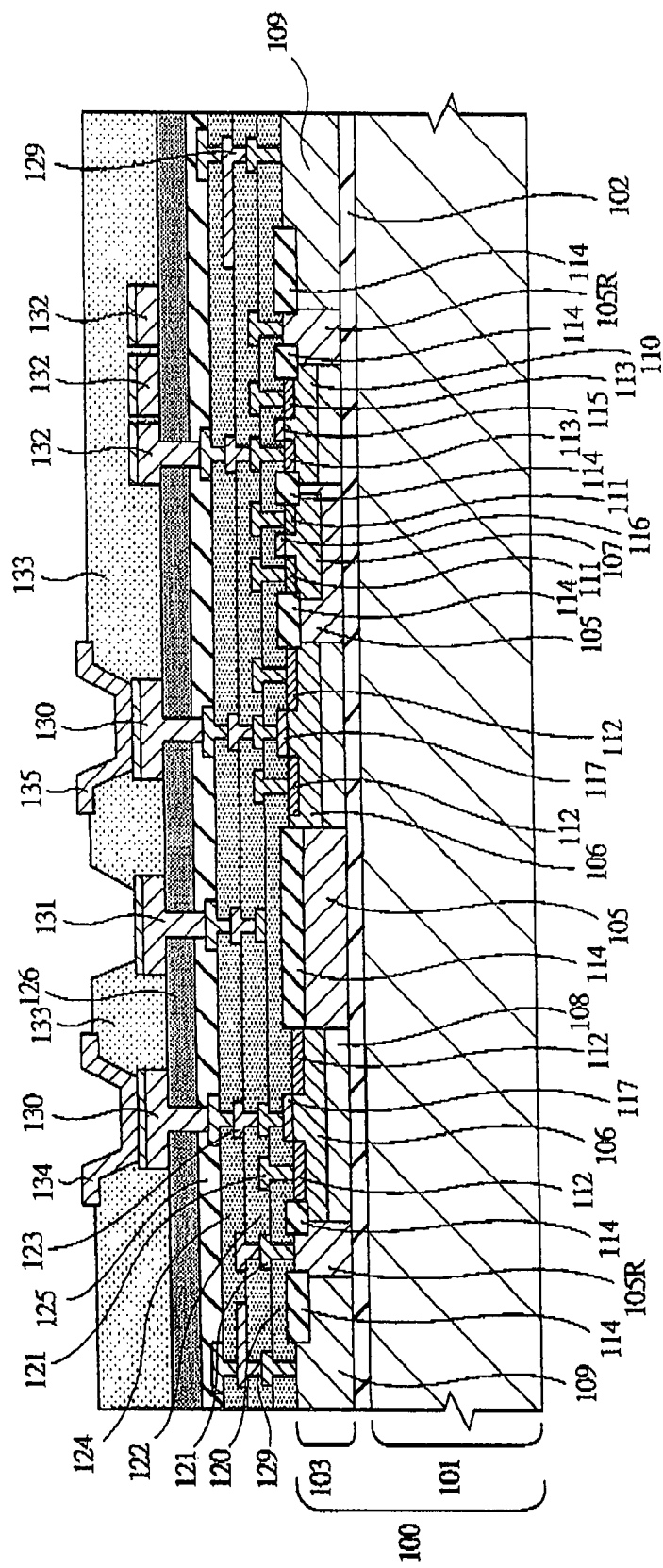
FIG. 9 is a cross-sectional view showing another structure of the sensor chip according to the present invention.

FIG. 9 is a cross-sectional view showing the third modified example of the device structure of the sensor chip. This structure is characterized in that metal wiring 129 is used to shut the diffusion path of the positive ions from the chip edge. In the outer region of the region in which the integrated circuit and the sensor are arranged, the diffusion path of positive ions of the interlayer insulating film made of silicon oxide is shut by using the metal wiring and the interlayer through hole. For example, the diffusion path of the positive ions can be shut by providing the ring-shaped wirings in the outer periphery of the chip and forming the ring-shaped through holes which connects the ring-shaped wirings in the different wiring layers. According to this structure, it is possible to achieve the structure that can shut the diffusion path of positive ions without any particular changes for the process of forming the normal MOS transistor. Note that it is also possible to combine the structure in which the path of positive ions is shut by the use of metal wiring and the structure in which the path of positive ions is shut by the use of an ion impermeable insulating film.

Similar to the device of FIG. 1, the electric insulation on the chip edge in the device of FIG. 9 is achieve by the pn junction composed of the guard ring 105R formed of an n type impurity layer fixed to the maximum potential and the p type impurity layer 109 with the floating potential. Alternatively, it is also possible to achieve the insulation by forming a deep trench structure in the periphery of the chip and using an ion impermeable insulating film similar to the structures of FIGS. 7 and 8.

The device structures of FIGS. 1, and 7 to 9 show the examples in which the first ISFET and the second ISFET having the ion sensitive films with different ion selectivities are provided. As described above, for example, in the structure shown in FIG. 1, since the well of the nMOS transistor is fixed to the power supply potential and the well of the PMOS transistor is fixed to the ground potential, it can be said that the influence of the positive ions diffused through the BOX layer is small. However, in the case of the structure of an amplifier for the constant drain voltage and the constant drain current as shown in FIG. 4, the n type well 108 in which the ISFET is formed is connected to the ground potential through the high-impedance current source 175 and is changed to the potential at which the drain current set by the current source 175 depending on the potential of the gate 170 of the ISFET can pass. More specifically, since the p well in which the ISFET is formed cannot be fixed to the ground potential, there is the possibility that it is influenced by the positive ions diffused from the BOX layer.

Figure 10:
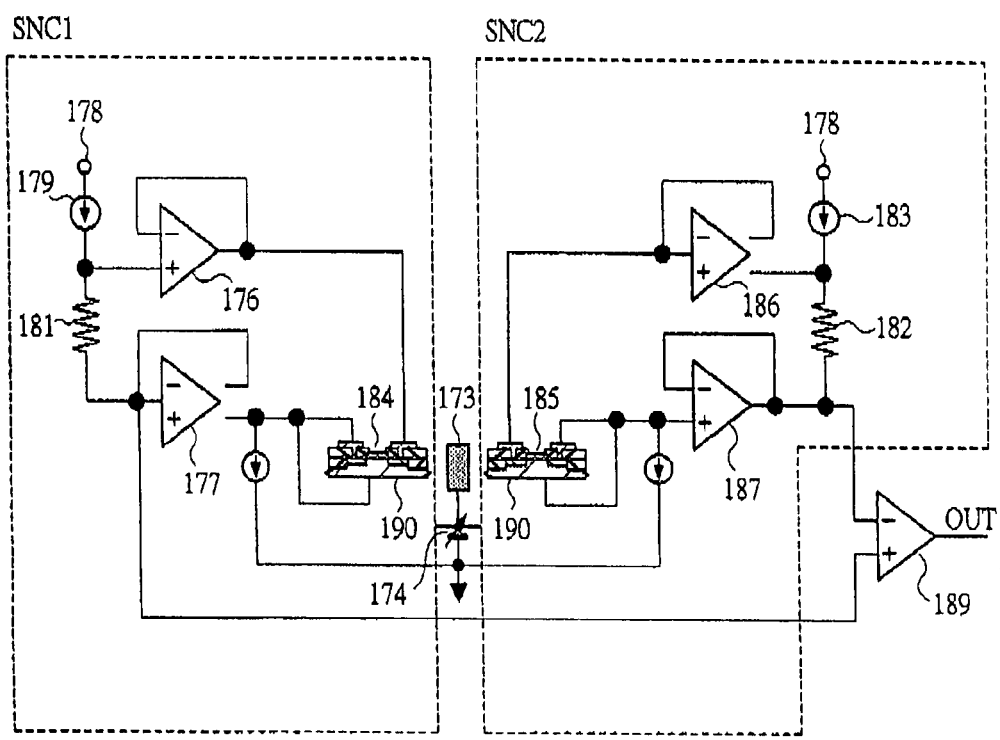
FIG. 10 is a block diagram showing another configuration of the sensor circuit using the ISFET.

Therefore, in order to further reduce the influence of the positive ions, the sensor circuit as shown in FIG. 10 is formed by using a reference ISFET 185. The sensor circuit in FIG. 10 is provided with a first sensor circuit SNC1 and a second sensor circuit SNC2, and they are operated by the common reference electrode 173 and bias voltage 174. The operation of the first and second sensor circuits SNC is similar to that of the sensor circuit in FIG. 4. Here, the ISFET 184 (first ISFET) of the first sensor circuit SNC1 is the measurement ISFET having a sensitive film which selectively captures the target ions and molecules, and the ISFET 185 (second ISFET) of the second sensor circuit SNC2 is the reference ISFET having a sensitive film with the selectivity for the ions and molecules different from those of the first ISFET 184. It is possible to cancel the influence of the positive ions by detecting the output difference between the first sensor circuit SNC1 and the second sensor circuit SNC2 by using a comparator 189. In FIG. 10, the reference character 182 denotes a resistor, 183 denotes a current source, 186 denotes an amplifier, and 187 denotes an amplifier.

Figure 11:
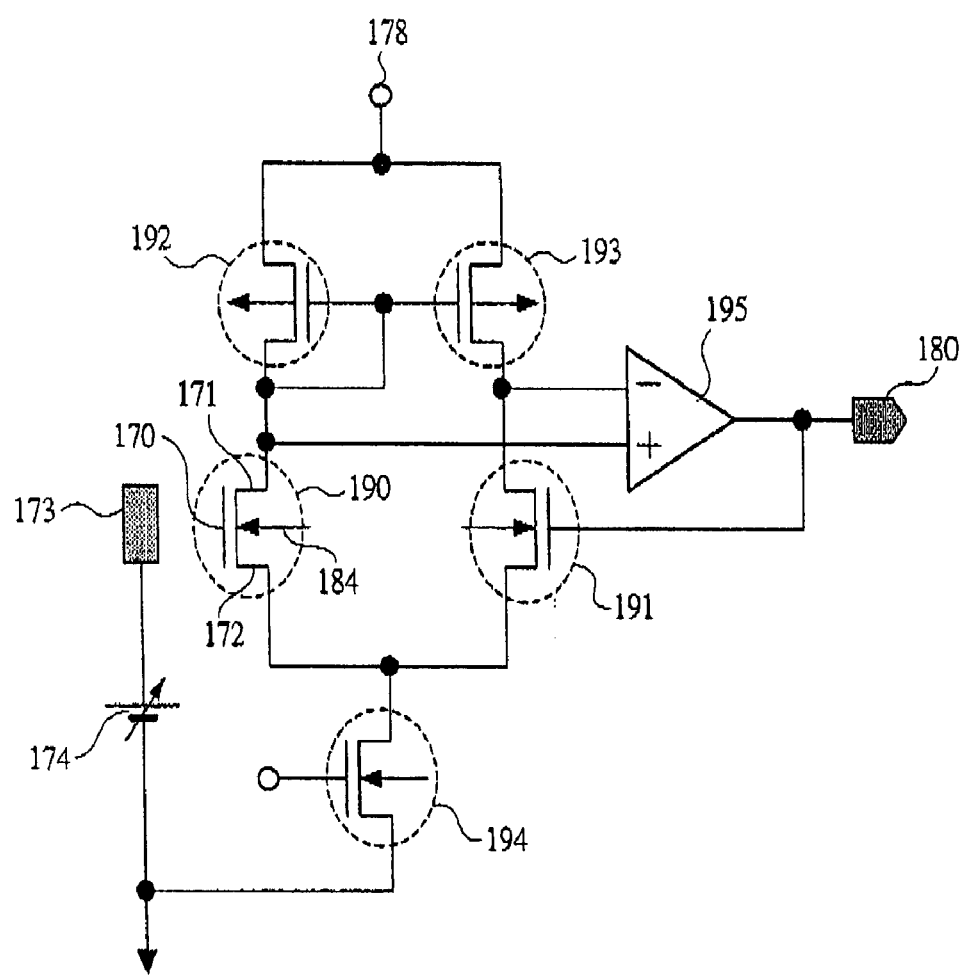
FIG. 11 is a block diagram showing another configuration of the sensor circuit using the ISFET.

As another circuit configuration, it is possible to use an amplifier with a differential pair as shown in FIG. 11. In the configuration of FIG. 4, since the well of the ISFET is set to floating, there is the possibility that the influence of the positive ions from the BOX layer is caused. Since the p type well potential is fixed to the ground potential in the configuration shown in FIG. 11, it is possible to eliminate the influence of the positive ions from the BOX layer. In FIG. 11, the reference character 191 denotes a MOS transistor comprising a differential pair coupled with ISFET, 192 and 193 denote MOS transistors comprising a current mirror for a differential amplifier, and 194 denotes a MOS transistor for a current source.

Figure 12A:
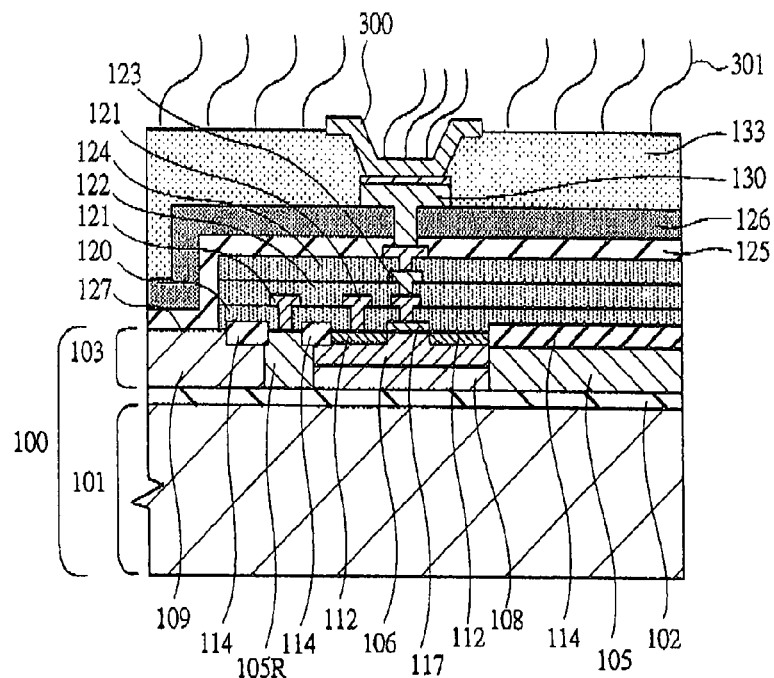
FIGS. 12A and 12B are cross-sectional views showing a part of the sensor (ISFET) of the sensor chip functioning as a DNA chip.
Figure 12B:
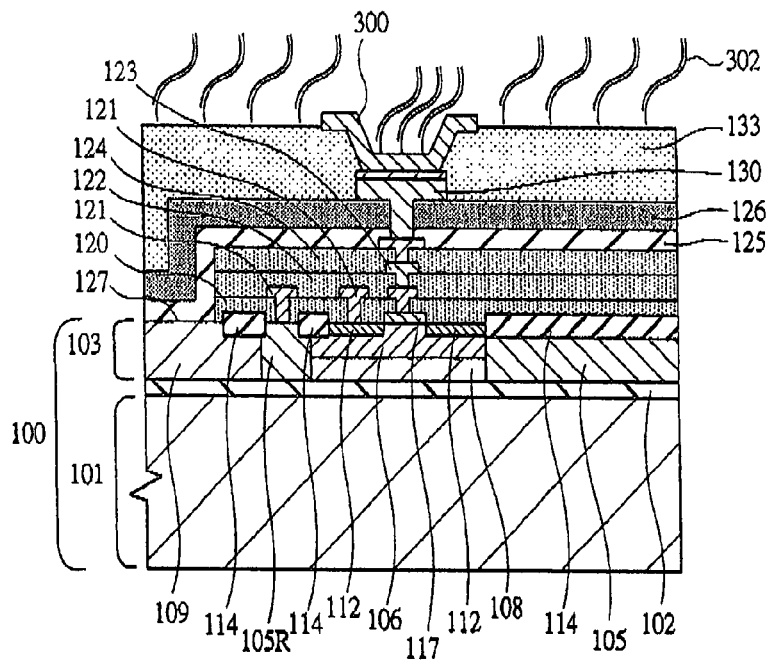

In the foregoing, the pH sensor is taken as an example in the description of the sensor chip according to the present invention. However, the sensor chip achieved by the present invention is not limited to the pH sensor. For example, the DNA sensor is also achieved in the same manner. FIG. 12 shows the partial structure of the ISFET in the case of the DNA sensor. In the case of the pH sensor, a sensitive film with the ion selectivity is deposited on the gate of the ISFET, whereas a metal layer 300 is deposited on the gate of the ISFET and a probe DNA 301 is attached to the metal layer 300 in the case of the DNA sensor. It is necessary that the metal layer 300 is formed of a material to which the probe DNA 301 can be easily attached. For example, gold is available. A target DNA 302 is bonded specifically to the probe DNA 301 of the DNA chip. Since the DNA has a negative charge, the potential of the ISFET is changed when the target DNA 302 and the probe DNA 301 are bonded specifically. By using this change, the existence of the target DNA 302 in the sample solution can be detected in the same manner as that of the pH sensor.

When forming the reference ISFET as shown in FIG. 10, two structures are available, that is, (1) a probe DNA with the base sequence different from that of the probe DNA of the measurement ISFET is attached onto the gate of the reference ISFET, and (2) the probe DNA is not attached onto the gate of the reference ISFET. From the viewpoint of the easiness of forming the device, the structure of (2) is more advantageous. In this case, the metal to which the probe DNA can be easily attached is used as the metal layer 300 for the gate of the measurement ISFET, and the metal to which the probe DNA is hardly attached is used for the gate of the reference ISFET.

Furthermore, it is also possible to detect an organic material such as protein by using the sensor chip according to the present invention. When protein does not have either of positive and negative charges, the preliminary process in which the protein to be detected is modified by the charge is performed in advance. By doing so, when the protein is specifically bonded to the ISFET due to the antigen-antibody reaction, the gate potential of the ISFET is changed. In this manner, it is possible to detect the organic material in the sample solution.

Figure 13A:
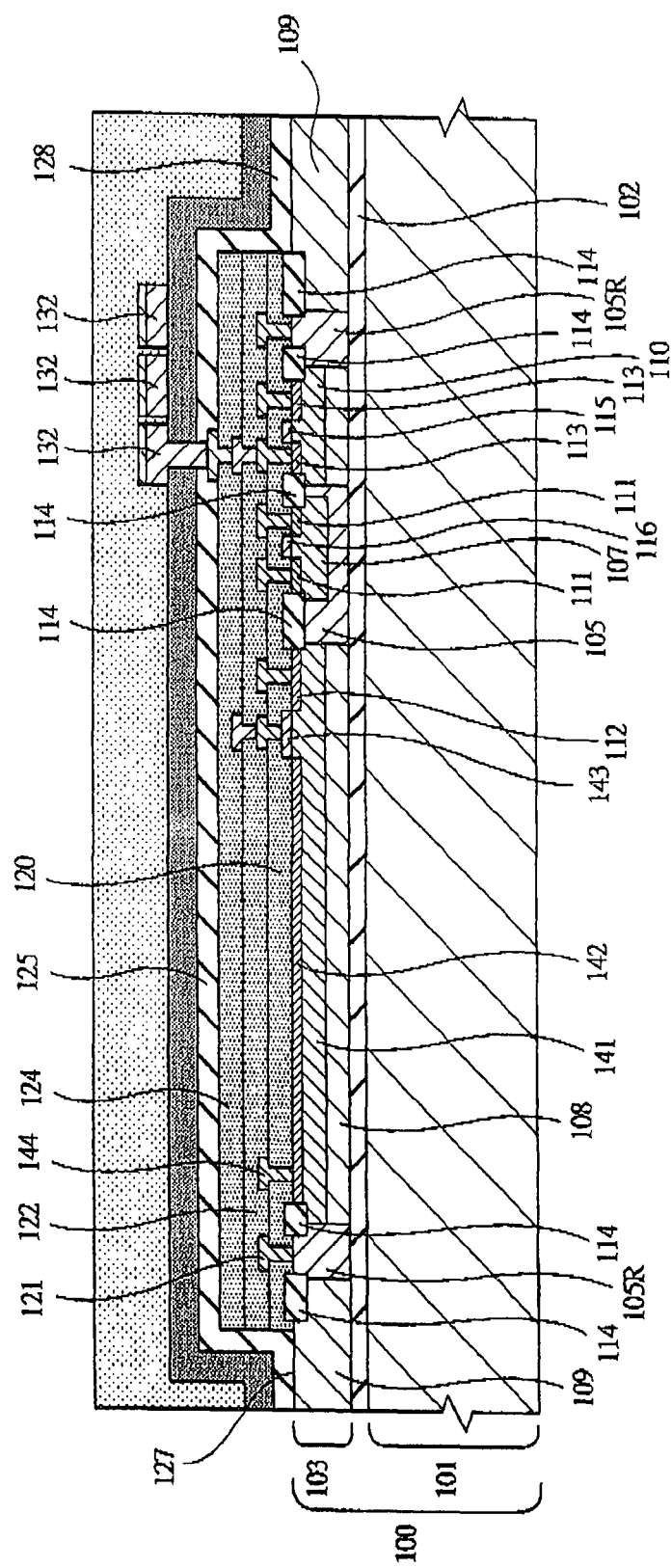
FIG. 13A is a cross-sectional view of the sensor chip using a photodiode as a sensor of the sensor chip.

Further, not only the ISFET but also other sensors such as a temperature sensor, a photodiode, and a strain sensor are also available. The structure of the sensor chip using the photodiode as a sensor is shown in FIG. 13A. The photodiode is formed of a p type layer 141 and an n type layer 142, and each circuit block described in FIG. 2 is integrated on the sensor chip. In FIG. 13A, the reference character 143 denotes a gate of MOS transistor for resetting a photodiode.

Figure 13B:
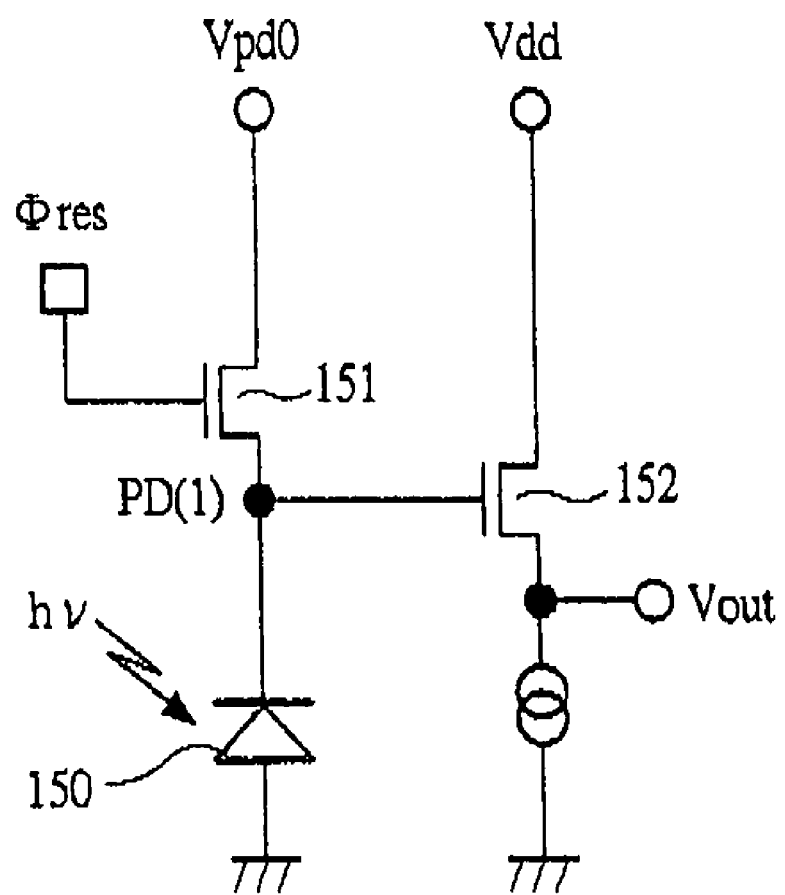
FIG. 13B is a circuit diagram showing an example of the light sensor circuit using the photodiode.

An example of the light sensor circuit using the photodiode is shown in FIG. 13B. First, $\phi$res is set in an on state (set to "H"). Thereby, the reset MOS transistor 151 connected to the photodiode 150 is turned on, and the node PD(1) is charged by the reset potential Vpd0. After the charge, the reset MOS transistor 151 is in an off state and the photodiode 150 is set to the charge storing mode to start the storage of the light signals from the sample. With the passage of time, the potential of the node PD (1) is gradually reduced from the reset potential Vpd0 depending on the incoming light amount. When the signal storage time has passed, the voltage reduction amount of the output node Vout is read via the source follower MOS transistor 152. In this manner, the light amount can be measured.

The photodiode can be used as the sensor of a measurement using bioluminescence such as the SNPs (single nucleotide polymorphisms analysis) of the DNA based on the HAMPER (Bioluminometry) method. In the BAMPER (Bioluminometric Assay with Modified Primer Extension Reactions) method, it is designed that the 3' end of the primer DNA is located at the position to detect the displacement and then the complementary strand synthesis is initiated. The complementary stand extension of the primer is significantly influenced by whether or not the 3' end matches with the target, and when it matches with the target, the complementary strand extension occurs. However, when it does not match with the target, the complementary strand extension scarcely occurs. The discrimination in SNPs is performed by using this. The chemical equation thereof is shown in FIG. 14.

More specifically, PPi (inorganic pyrophosphate) is formed as the by-product of the DNA corrplementary strand synthesis of the reaction substrate dNTP (deoxynucleotide triphoshoate) in the presence of the DNA polymerase. When this is reacted in the presence of APS (adenosine 5 phosphosulfate) and ATP sulfurylase, the ATP is produced. Since the ATP emits a light when it is reacted in the presence of luciferin and luciferase, the complementary strand extension is detected by measuring the light. Since the inorganic pyrophosphate is produced by the light-emitting reaction, the light emission is continued while consuming the APS. The light emission resulting from the complementary strand extension is detected by the photodiode.

An example of the process flow for forming the structure of FIG. 1 is shown in FIGS. 15A to 15G. FIGS. 15A to 15G are cross-sectional views each showing the step of the manufacturing process.

Figure 15A:
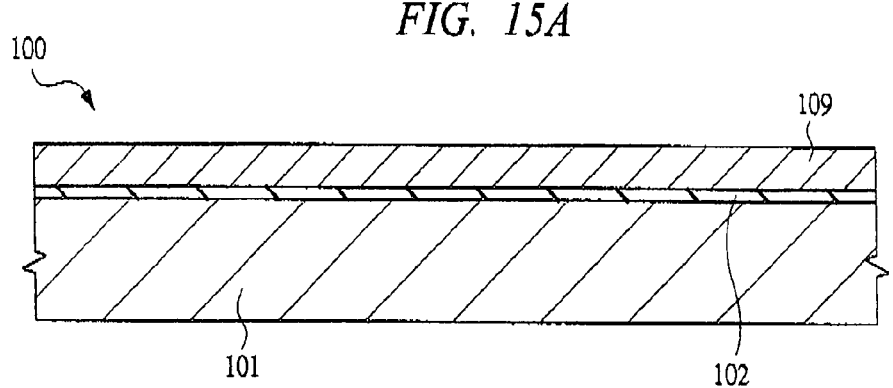
FIGS. 15A to 15G are cross-sectional views showing the process flow for manufacturing the sensor chip of FIG. 1.

In the step of FIG. 15A, an SOI substrate for forming the device is formed. Here, the thickness of the BOX layer is 0.5 μm, and the conductivity type of a silicon layer on the BOX layer is p type, the specific resistance thereof is 10 Ωcm, and the thickness thereof is 1.5 μm.

Figure 15B:
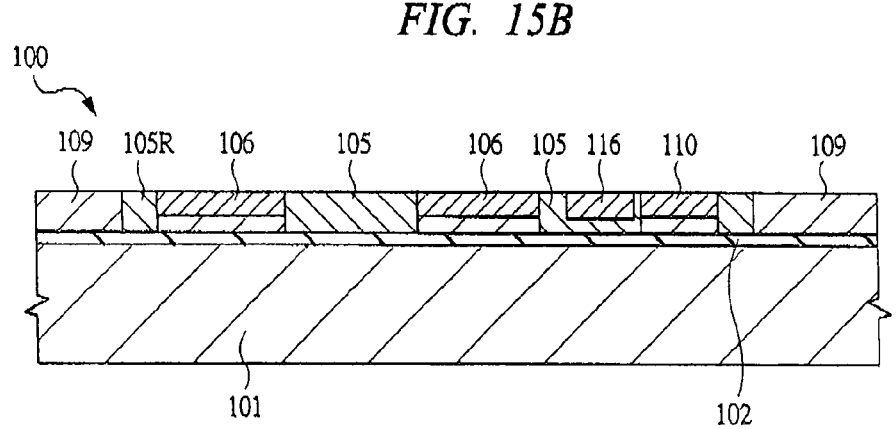

In the step of FIG. 15B, a field insulating film for the device isolation is formed. A silicon nitride film is patterned so as to determine the region of the field insulating film. The oxide film is formed by the thermal treatment at 110° C. in the wet oxidizing atmosphere. The oxidation time is controlled so that the oxide film has the thickness of 450 nm.

Figure 15C:
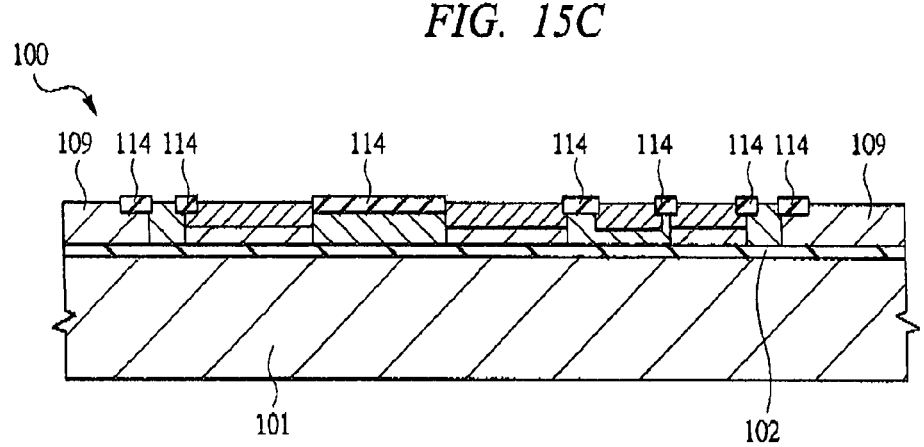

In the step of FIG. 15C, windows of resist are formed in the isolation region between the wells and the insulation region around the chip. Thereafter, phosphorus ions are implanted for forming a deep n type impurity diffusion layer which reaches the BOX layer and the diffusion at 1200° C. for 120 minutes is performed. Subsequently, the resist is patterned and boron/phosphorus which are the impurities of the p/n type wells are ion-implanted. Thereafter, the thermal diffusion at 1100° C. for 50 minutes is performed.

Figure 15D:
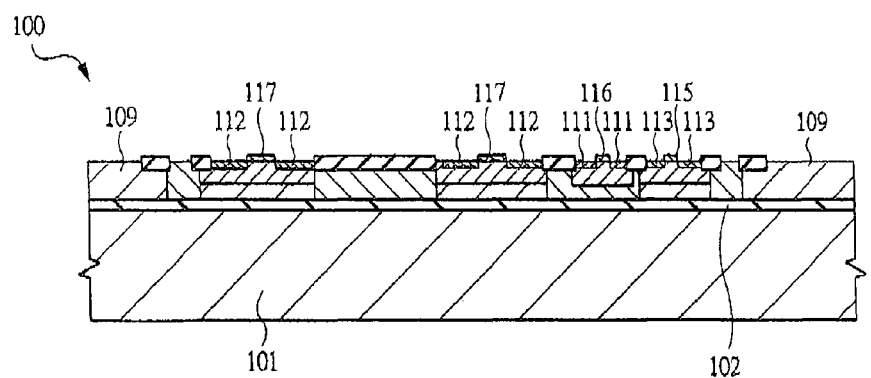

In the step of FIG. 15D, a MOS transistor is formed. First, $BF_2$ for adjusting the threshold voltage is ion-implanted. Next, an oxide film with a thickness of 25 nm is to be the gate insulating film of the high breakdown voltage MOS transistor is formed by the thermal treatment in the wet oxidizing atmosphere at 850° C. Subsequently, the high breakdown voltage gate oxide film located at the position where a normal breakdown voltage MOS transistor is to be formed is removed and a gate oxide film with a thickness of 8 nm is formed by the thermal treatment at 800° C. in the wet oxidizing atmosphere. Then, polysilicon and tungsten silicide to be the gate are deposited and processed into the shape of the gate. Thereafter, as the impurity for relaxing the electric field, phosphorus is ion-implanted into the NMOS region and boron is ion-implanted into the pMOS region, and then, the thermal treatment at 850° C. for 10 minutes is performed. In order to form a high-concentration impurity layer to be the source and drain, arsenic is ion-implanted into the NMOS region and $BF_2$ is ion-implanted into the pMOS region, and then, it is annealed at 850° C. for 20 minutes.

Figure 15E:
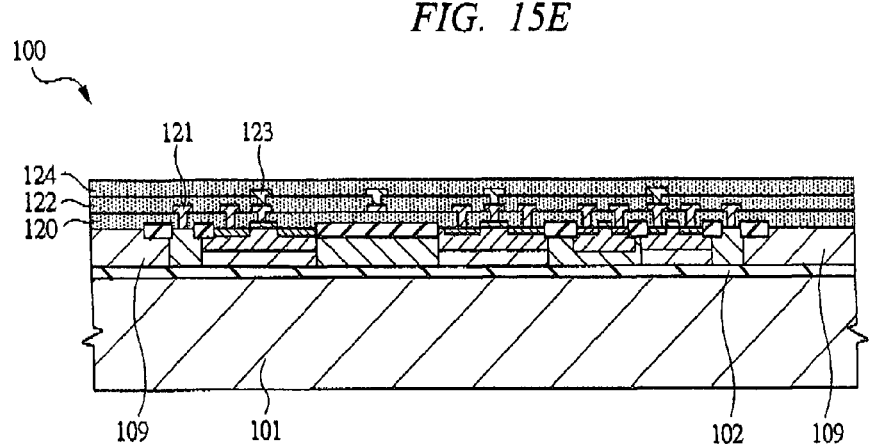

In the step of FIG. 15E, a wiring and an interlayer insulating film are formed. First, a first layer wiring is formed and then a silicon nitride layer and a silicon oxide layer to be the insulating films with the MOS transistor are deposited. Thereafter, the patterning for forming the contact holes is performed. Subsequently, a barrier layer made of titanium nitride and tungsten is deposited, and thereafter, aluminum is deposited and patterned to form the wiring. Next, as an insulating film with a second layer wiring, a silicon oxide film is deposited and through holes for connecting the wirings are formed, and then, a barrier layer made of titanium nitride and tungsten is deposited. Thereafter, aluminum is deposited and patterned to form the wiring. Then, a third layer wiring is formed in the same manner.

Figure 15F:
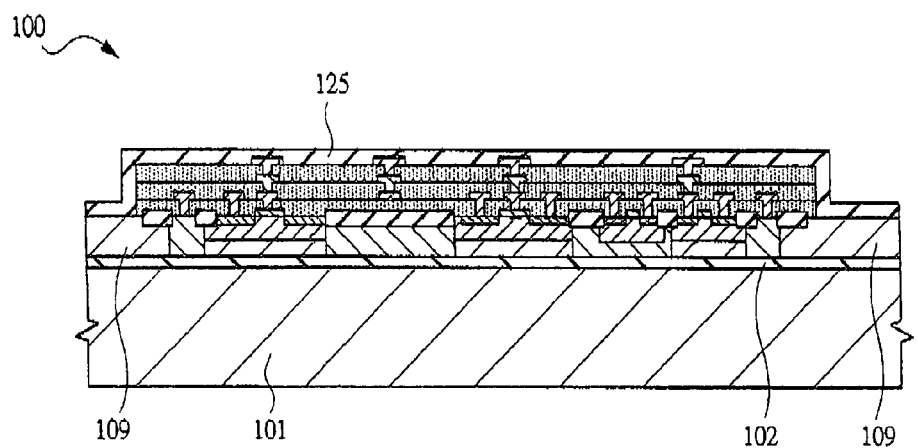

In the step of FIG. 15F, a silicon nitride film is formed as a protection film (ion impermeable film), the patterning of the pad portion for the coil is performed and then the passivation film on the pad is removed.

Figure 15G:
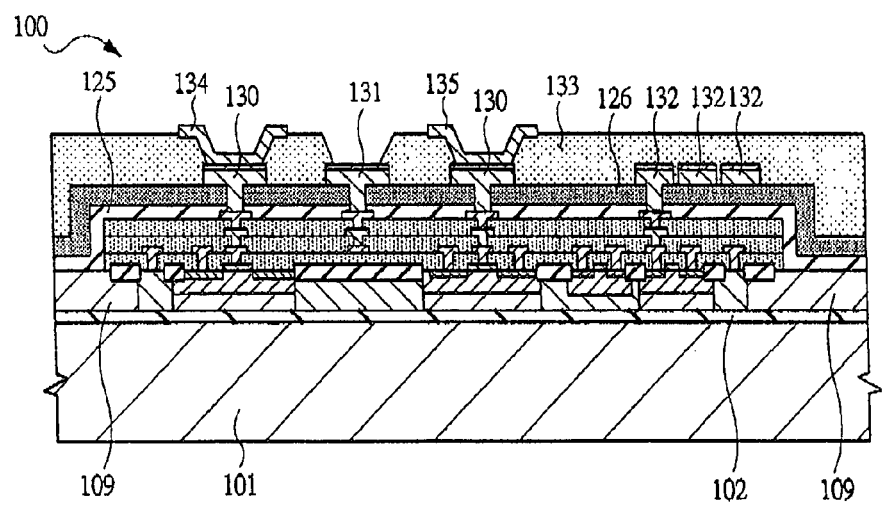

In the step of FIG. 15G, copper to be the communication coil is formed by plating. The ion sensitive film is formed in the openings connected to the gate of the ISFET according to need.

The present invention can be applied to a sensor chip for easily examining a biological material such as gene and physical-chemical quantity and to a measurement system for performing the examination by using the sensor chip.

What is claimed is:

1. An unpackaged semiconductor integrated circuit device used in a solution, and having an SOI substrate in which a support substrate supports a buried insulating layer and a semiconductor layer, and an integrated circuit is formed on said semiconductor layer, comprising:
   a guard ring layer which is formed with an n-type impurity diffusion layer in said semiconductor layer and which surrounds a formation area of said integrated circuit, said guard ring layer reaching said buried insulating layer and being in connection with a node having a maximum potential of said integrated circuit; and
   a floating layer which is formed with a p-type impurity diffusion layer in said semiconductor layer and which surrounds said guard ring layer, an inside surface of said floating layer being in contact with an outside surface of said guard ring layer, and said floating layer reaching an outer surface of said semiconductor layer, said outer surface of said semiconductor layer being exposed to said solution.

2. The unpackaged semiconductor integrated circuit device according to claim 1,
   wherein said integrated circuit includes an ion sensitive field effect transistor and an ion sensitive film which is electrically connected to a gate of said ion sensitive field effect transistor, and
   wherein, when said unpackaged semiconductor integrated circuit device is used, said ion sensitive film is exposed to said solution instead of said outer surface of said semiconductor layer.

3. The unpackaged semiconductor integrated circuit device according to claim 1,
   wherein said integrated circuit includes a first ion sensitive field effect transistor, a second ion sensitive field effect transistor, a first ion sensitive film electrically connected to a gate of said first ion sensitive field effect transistor, and a second ion sensitive film electrically connected to a gate of said second ion sensitive field effect transistor,
   wherein, an ion selectivity of said first ion sensitive film is different from an ion selectivity of said second sensitive film, and
   wherein, when said unpackaged semiconductor integrated circuit device is used, said first and second ion sensitive films are exposed to said solution instead of said outer surface of said semiconductor layer.

4. The unpackaged semiconductor integrated circuit device according to claim 1,
   wherein said integrated circuit includes an ion sensitive field effect transistor, a metal layer which is electrically connected to a gate of said ion sensitive field effect transistor and a probe DNA attached to said metal layer, and
   wherein, when said unpackaged semiconductor integrated circuit device is used, said metal layer and said probe DNA are exposed to said solution instead of said outer surface of said semiconductor layer.

5. An unpackaged semiconductor integrated circuit device used in a solution, and having an SOI substrate in which a support substrate supports a buried insulating layer and a semiconductor layer, and an integrated circuit being formed on said semiconductor layer, comprising:
   a guard ring layer which is formed with a p-type impurity diffusion layer in said semiconductor layer, and which surrounds a formation area of said integrated circuit, said guard ring reaching said buried insulating layer and being in connection with a node having a minimum potential of said integrated circuit; and
   a floating layer which is formed with an n-type impurity diffusion layer in said semiconductor layer, and which surrounds said guard ring layer, wherein an inside surface of said floating layer is in contact with an outside surface of said guard ring layer, said floating layer reaching an outer surface of said semiconductor layer, said outer surface of said semiconductor layer being exposed to said solution.

6. The unpackaged semiconductor integrated circuit device according to claim 5,
   wherein said integrated circuit includes an ion sensitive field effect transistor and an ion sensitive film which is electrically connected to a gate of said ion sensitive field effect transistor, and
   wherein, when said unpackaged semiconductor integrated circuit device is used, said ion sensitive film is exposed to said solution instead of said outer surface of said semiconductor layer.

7. The unpackaged semiconductor integrated circuit device according to claim 5,
   wherein said integrated circuit includes a first ion sensitive field effect transistor, a second ion sensitive field effect transistor, a first ion sensitive film electrically connected to a gate of said first ion sensitive field effect transistor, and a second ion sensitive film electrically connected to a gate of said second ion sensitive field effect transistor,
   wherein, an ion selectivity of said first ion sensitive film is different from an ion selectivity of said second sensitive film, and
   wherein, when said unpackaged semiconductor integrated circuit device is used, said first and second ion sensitive films are exposed to said solution instead of said outer surface of said semiconductor layer.

8. The unpackaged semiconductor integrated circuit device according to claim 5,
   wherein said integrated circuit includes an ion sensitive field effect transistor, a metal layer electrically connected to a gate of said ion sensitive field effect transistor and a probe DNA attached to said metal layer, and
   wherein, when said unpackaged semiconductor integrated circuit device is used, said metal layer and said probe DNA are exposed to said solution instead of said outer surface of said semiconductor layer.

* * * * *